| United States Patent [19] | [11] | 4,404,181 |
|---|---|---|
| Mauthner | [45] | Sep. 13, 1983 |

[54] EXTENDED-LIFE TISSUE FIXATIVE COMPOSITION AND METHOD OF USING THE SAME

[75] Inventor: Thomas Mauthner, Livonia, Mich.

[73] Assignee: Cambridge Chemical Products, Inc., Ft. Lauderdale, Fla.

[21] Appl. No.: 311,682

[22] Filed: Oct. 15, 1981

[51] Int. Cl.$^3$ .......................... G01N 1/28; A01N 1/02; A61K 35/12; C12N 5/00
[52] U.S. Cl. .......................................... 424/3; 424/75
[58] Field of Search ...................................... 424/3, 75

[56] References Cited

U.S. PATENT DOCUMENTS 3,057,775  10/1962  Rendon ................................ 424/3 X
3,257,279   6/1966  Schain ...................................... 424/3
3,862,300   1/1975  Wertlake ................................... 424/3
3,900,558   8/1975  Kinsolving ............................. 424/12

Primary Examiner—Anna P. Fagelson
Attorney, Agent, or Firm—Krass, Young & Schivley

[57] ABSTRACT

Extended-life aqueous tissue fixative compositions or solutions are provided for use in histopathology work and the like. The compositions include glutaraldehyde at controlled pH, a boric acidtetraborate buffer, buffer stabilizer and complexing agent. The compositions, which also may include a compatible surfactant, and their method of application enable efficient fixing such that the treated tissues have low artifactual color and good texture and may readily be sectioned and accurately stained.

14 Claims, No Drawings

EXTENDED-LIFE TISSUE FIXATIVE COMPOSITION AND METHOD OF USING THE SAME

DESCRIPTION

1. Technical Field

This invention relates to the preparation of tissue specimens for analytical evaluation. More particularly the invention relates to methods and compositions useful in the fixing and preservation of tissue for purposes of histopathological examination and the like.

2. Background Art

For over a century, tissue fixative compositions used to preserve and prepare tissue for analytical evaluation have been based on formaldehyde. The standard composition employed for tissue preservation and the preparation of thin-cut tissue for microscopic examination is Formalin. Formalin is a 3 to 10 percent solution of formaldehyde in water, usually containing about 15 percent methyl alcohol. Alcohol improves the preservative properties of the solution. Despite numerous disadvantages, most notably high toxicity and irritant properties, Formalin remains the fixative of choice in typical laboratory applications owing to its rapid reaction with exposed tissue surfaces and consequent maximized cellular preservation. Methanol may adversely affect the texture of the tissue, rendering it too brittle or, more usually, too soft for ease in cutting for slide preparation. It also may produce pigmented artifacts or impurities which interfere with staining. Formalin containing methanol nevertheless provides preserved tissue which can be satisfactorily sectioned and stained for microscopic examination.

Owing primarily to the high toxicity of Formalin (see, for example, "A Firing Over Formaldehyde", Science, 213, pages 630-631, 1981), various substitutes have been proposed in the past. Glutaraldehyde, in particular, has been investigated, for its preservative properties and relatively low toxicity. Specific glutaraldehyde solutions have, to some extent, been accepted in specialized applications, such as tissue fixatives for use in electron microscopy. However, glutaraldehyde has not been favored in standard laboratory applications, primarily because known glutaraldehyde solutions are slow to react with exposed tissue surfaces, permitting deterioration prior to fixation. Further, tissue treated with glutaraldehyde solutions typically have a poor texture unsuitable for sectioning and take staining poorly. Additionally, glutaraldehyde solutions are inherently unstable, decomposing on standing within short periods of time. While the instability of glutaraldehyde solutions has previously been attributed to acidity thereof, attempts to solve this problem have been generally limited to the use of phosphate-based buffer systems such as monopotassium and disodium phosphates. These phosphate-buffer solutions also have remained stable for only short periods.

Accordingly, it is an object of this invention to provide a tissue fixative composition which has relatively low toxicity and a long shelf life.

It is another object of the invention to provide a composition for fixing tissue for light microscopy which provides a firm tissue section easily cut to the desired thickness.

It is a further object to provide a tissue fixative composition for use in histopathological applications which rapidly penetrates tissue surfaces for maximum cellular preservation, leaves minimal pigmented artifacts, and permits accurate staining.

It is still another object, for purposes of tissue staining, to provide a method of preparing the surface of the tissue for better and faster absorbency of various stains and dyestuffs used in histopathology and related fields.

These and other objects, features and advantages will be seen from the following summary and detailed description of the invention.

SUMMARY AND DETAILED DESCRIPTION OF THE INVENTION

The invention in one aspect concerns an extended-life aqueous tissue fixative composition or solution. The composition, having a good shelf life over a wide temperature range, comprises in admixture glutaraldehyde at controlled pH, a boric acid-borate buffer, a buffer stabilizer which may be one or more water soluble ascorbic acid compounds, a metal complexing agent which may be one or more citric acid compounds, and optionally a surfactant substance or substances. For a ready-to-use preparation, the composition may contain about 5.5 to about 10% and preferably about 7.5 to about 8.5%, by weight of glutaraldehyde in water. The ready-to-use composition is constituted at acid or neutral pH, specifically in the range from about 5.8 to about 7.0, preferably from 6.2 to 6.8 and for best results from 6.4 to 6.5, suitably by mixing the glutaraldehyde solution with a pH adjusting reagent which may include an acid such as citric acid and/or an alkaline reagent or base such as sodium hydroxide. The composition at the selected pH is then buffered with a boric acid-borate salt buffer sufficient in amount to keep the composition at the selected pH for prolonged periods. A preferred buffer is boric acid-sodium tetraborate decahydrate ($Na_2B_4O_7 \cdot 10H_2O$) in an amount from about 0.12 to about 0.6% by weight of boric acid and from about 0.01 to about 0.1% by weight of sodium tetraborate decahydrate. The stabilizer is ascorbic acid or a water soluble ascorbic acid salt compound or mixture of such compounds in an amount sufficient to stabilize the buffer. Suitably, the stabilizer may be free ascorbic acid or its alkali metal (sodium or potassium) salt. Expressed as ascorbic acid content, one may conveniently use about 0.1 to about 0.8% by weight based on the total weight of the composition. The metal complexing agent serves to tie up or inactivate interfering metals such as iron. It also serves as a secondary buffer, contributing to the speed of fixation and staining. The complexing agent, as indicated, may be citric acid or water soluble citric acid salt such as the alkali metal (sodium or potassium) salt which in the formulation is constituted as the free acid/citrate salt. The range for the complexing agent expressed as sodium citrate suitably is about 0.06 to about 1.0%. A preferred tissue fixative solution is one comprising the following constituted components in amounts expressed as approximate percent by weight based on total weight of the solution:

| | |
|---|---|
| Glutaraldehyde | 5.5 to 10.0 |
| Sodium hydroxide | 0.012 to 0.06 |
| Sodium tetraborate.10H$_2$O | 0.010 to 0.1 |
| Boric acid | 0.120 to 0.6 |
| Ascorbic acid | 0.100 to 0.8 |
| Sodium citrate | 0.06 to 1.0 |
| Water | Balance |

The optional surfactant component referred to above co-acts to provide several advantages including rapid tissue fixation, more complete absorption of tissue staining, and reduction of artifacts that interfere with the evaluation of tissue staining. The surfactant employed is one or more solution soluble $C_{5-11}$ fatty acids and fatty acid salts. Sufficient surfactant is employed to provide in the finished solution a surface tension in the range from about 7 to about 20, and preferably 10 to 15, dynes per centimeter. As indicated, the resulting low surface tension solution advantageously prepares the surface of tissues for superior absorbence of the usual staining material. Preferred surfactants are the $C_{6-8}$ fatty acid compounds, especially the n-caproic, heptanoic, and caprylic (octanoic) acid salt compounds, especially the sodium salt compounds. A preferred tissue fixative solution containing surfactant is one having the following formulation:

| Component | Percent by Weight Based on Total Weight of Composition |
|---|---|
| Glutaraldehyde | 5.5 to 10.0 |
| Sodium hydroxide | 0.012 to 0.06 |
| Sodium Tetraborate.10H$_2$O | 0.010 to 0.1 |
| Boric Acid | 0.120 to 0.6 |
| Ascorbic Acid | 0.100 to 0.8 |
| Sodium Citrate | 0.060 to 1.0 |
| $C_{7-8}$ fatty acid, sodium salt | 0.050 to 0.5 |
| Water | Balance |

The surface tension of the tissue fixative solution of the invention varies with the quantity of surfactant present. This is illustrated by adding varying amounts of surfactant to a preferred stock solution having an interfacial surface tension of 35.6 dynes per centimeter formulated as shown in Table I. The resulting effect on surface tension is shown in Table II; pH of the solution is adjusted to 6.40 where necessary.

TABLE I

| Tissue Fixative Solution Without Surfactant | |
|---|---|
| Component | Wt. % |
| Glutaraldehyde | 8.000 |
| Sodium Hydroxide | 0.012 |
| Sodium Tetraborate | 0.010 |
| Boric Acid | 0.120 |
| Ascorbic Acid | 0.100 |
| Sodium Citrate | 0.060 |
| Water | Balance |

TABLE II

| Tissue Fixative Solution With Surfactant | | |
|---|---|---|
| Surfactant | Concentration (Wt. %) | Surface Tension |
| Heptanoic Acid | 0.001 | 20.0 |
| Heptanoic Acid | 0.050 | 14.6 |
| Heptanoic Acid | 0.100 | 8.4 |
| Caprylic (octanoic) Acid | 0.001 | 21.6 |
| Caprylic Acid | 0.050 | 14.4 |
| Caprylic Acid | 0.100 | 11.0 |

For a storage stable product that is dilutable with water to a lower glutaraldehyde content (e.g., dilutable from 30 to 35% down to 5.5 to 10%) for use after storage, the composition of the invention can be made up as a concentrate containing the several components in correspondingly high concentration at a pH in the range from about 5.8 to about 7.0 and preferably 6.2 to 6.8 such that, upon dilution with water to a ready-to-use product form, the individual components are within the limits described above for a ready-to-use fixative solution. For example a formulation suitable as a storage-stable concentrate, at pH 6.5 dilutable as one part with 3 parts of water to provide a ready-to-use fixative solution, is the following:

| Component | Percent by Weight |
|---|---|
| Glutaraldehyde | 32.5 |
| NaOH | 0.026 |
| Na$_2$B$_4$O$_7$.10H$_2$O | 0.030 |
| Boric Acid | 0.288 |
| Sodium citrate anhyd. | 0.056 |
| Ascorbic acid | 0.300 |
| Sodium caprylate | 0.150 |
| Water | Balance |

The invention in another aspect concerns a method of preparing tissue for cutting, staining and/or microscopic evaluation wherein specimen tissue prior to dehydration is subjected to preservation with a storage stable aqueous tissue fixative solution of the invention, formulated as described above. Thus, the solution comprises glutaraldehyde at controlled pH, a boric acid-borate buffer, a buffer stabilizer and a metal complexing agent as described above, and an optional surfactant. A preferred embodiment is the method wherein the tissue fixative solution is a ready-to-use solution prepared by dilution with water of a storage stable dilutable tissue fixative concentrate. These methods advantageously avoid the use of the relatively more toxic and irritant substance, formaldehyde or the use of substances which result in treated tissues that are difficult to section or are artifactually pigmented. The methods also allow the user to select the desired extent of dilution required for specific objectives without the need for point-of-use adjustment of pH or addition of buffer agents, stabilizers, etc.

The invention is illustrated by the following examples.

EXAMPLE I—SOLUTION A

A fixative solution according to the invention is prepared by admixing the following components in the amounts indicated:

| Component | Percent by Weight |
|---|---|
| Water | 91.56 |
| Glutaraldehyde | 8.0 |
| Sodium Hydroxide | 0.012 |
| Sodium Tetraborate | 0.01 |
| Boric Acid | 0.12 |
| Ascorbic Acid | 0.10 |
| Sodium Citrate Anhyd. | 0.06 |
| Sodium Caprylate (octanoate) | 0.050 |

EXAMPLE II

A solution having a different surfactant but similarly effective is prepared by the procedure of Example I in which sodium caprylate is replaced by sodium heptanoate.

EXAMPLE III—STORAGE STABILITY

The solution of Example I (Solution A) can be compared for storage stability at room temperature with an 8.0% aqueous solution of commercial grade glutaraldehyde (Solution B) and an 8.0% solution of commercial grade glutaraldehyde buffered to pH 6.6 with a phosphate buffer system comprising disodium phosphate and monopotassium phosphate (Solution C). At the end of each test period aliquots of the test Solutions A, B and C are analyzed by a standard procedure (Union Carbide Publication No. TT-TL-2016) for glutaraldehyde content. Typical results are given in Table III. Percentages refer to weight percent of glutaraldehyde present in the test solution after each test period.

TABLE III

| | 8% Glutaraldehyde Solutions Stability At Room Temperature | | | |
|---|---|---|---|---|
| | After 90 Days | After 180 Days | After 360 Days | After 450 Days |
| Solution A (Example I) | 7.8% | 7.8% | 7.5% | 7.3% |
| Solution B | 5.4% | 4.8% | Precipitation | |
| Solution C | 7.5% | 6.9% | 5.2% | Not tested |

These results show that conventional glutaraldehyde solutions are unsatisfactory when kept in storage for relatively short periods. Thus, Solution B is unsatisfactory after 90 days storage. Solution C is unacceptably low in glutaraldehyde content after 180 days. After 150 days it shows signs of decomposition by color change and develops a slight amount of precipitate. Solution A remains acceptable throughout storage; it stays clear and shows no physical signs of deterioration. The surface tension of Solution A when made up and after 360 days of storage is 14.4 and 14.7 dynes per cm., respectively.

EXAMPLE IV

STORAGE STABILITY AT ELEVATED TEMPERATURE

The storage stability test of Example III in a typical run confirms the stability of Solution A at elevated temperature conditions (30° to 32° C. for 360 days). The loss of glutaraldehyde is 9.2% of the original assay. The loss is commercially acceptable. No polymerization with precipitation occurs. It is important, however, when extended storage is contemplated, that excess glutaraldehyde is included in the formulation in an amount that will offset the contemplated gradual loss by decomposition with time.

EXAMPLE V

COMPARISON OF BUFFERED GLUTARALDEHYDE SOLUTIONS

A phosphate-buffered glutaraldehyde solution is prepared by buffering an 8.0% glutaraldehyde solution to pH 6.8 with 0.64 g. of disodium phosphate and 0.52 g. of monosodium phosphate per 100 ml. of solution. When stored at room temperature the pH remains at 6.8 for 20 days and then slowly drops. At 120 days the pH of the solution is 5.9. Discoloration of the solution and precipitation are observed.

By contrast, a comparable borate-buffered solution prepared by admixing the following components:
100 ml 8.0% Glutaraldehyde
    0.012 g of Sodium Hydroxide
    0.010 g of Sodium Tetraborate.10 H$_2$O
    0.120 g of Boric Acid
    0.10 g of Ascorbic Acid and adjusting with sodium hydroxide to pH 6.40, is stable when stored 420 days. When examined at 90 day intervals it remains substantially constant, and no discoloration or precipitation is observed.

EXAMPLE VI—STAINING

The glutaraldehyde solution prepared as described in Example I is employed to fix tissue in the following process employing an Autotechnicon apparatus: Replicate specimen tissues, each measuring about 2 sq. cm. and of a maximum thickness of 0.5 cm. are first immersed in the solution of Example I at room temperature for 5 hours, and then transferred into fresh solution for an additional hour. Dehydration is begun by immersing the resulting fixed specimens in 95% ethyl alcohol for 1 hour; transferring the same into absolute (100%) ethyl alcohol for 1 hour and next in fresh xylene for another hour. The tissues are then sealed in paraffin for at least 1 hour, cut to 4–5 micron thickness and stained. The resulting tissues, even those that are typically difficult to fix, are properly fixed, do not show brittleness, and are easy to cut and stain. Malignant and benign tissues typically display excellent fixation with good staining characteristics and cellular preservation. The fixative solution of Example I exhibits rapid penetration of tissues with minimal amounts of artifacts; staining of the thus fixed tissues displays excellent histologic and cytologic detail. Specifically, staining performed on the 4–5 micron sections fixed and prepared as described, using Hexatoxylin-Eosin, Gomori's Trichrome stain and Periodic Acid-Schiff (PAS), are at least equal in quality to comparable sections prepared using the conventional formaldehyde fixative. In many cases the cytologic detail and staining qualities of the tissues fixed in the solution of Example I is superior to those of the same types of tissues fixed in 10% Formalin. Extended testing demonstrates that glandular tissue, nerve tissue, brain and dense connective tissue fixed according to the invention show good staining qualities and appear well perserved with distinct cytoplasmic and nuclear outline. An important advantage of the tissues fixed in the solution of Example I is the absence of pigment artifacts frequently seen when sections are fixed in buffered Formalin.

EXAMPLE VII

TISSUE FIXATIVE CONCENTRATE SOLUTION

A stable, concentrated fixative solution according to the present invention is prepared by the procedure of Example I by admixing the following ingredients (parts by weight):

| | |
|---|---|
| Glutaraldehyde | 32.5 |
| Sodium Hydroxide | 0.026 |
| Sodium Tetraborate.10H$_2$O | 0.030 |
| Boric Acid | 0.288 |
| Sodium Citrate anh. | 0.056 |
| Ascorbic Acid | 0.300 |
| Sodium Caprylate | 0.150 |
| Water | Balance |

This solution, when one part is diluted with three parts deionized water, exhibits the same properties as the solutions of Examples I and II.

Extended storage demonstrates that the solution concentrate is stable. For example when equal portions of concentrate are stored in polyethylene containers for 450 days, one portion at 20° C. and one portion at 30°

C., the loss of glutaraldehyde is nominal, viz.: 7.2% and 8.0%, respectively. Another portion diluted with three portions of deionized water is stable for 360 days at 20° C. The solutions, even though kept for an extended period simulating conditions of commercial storage, have fixing and staining properties substantially identical to a freshly-prepared solution of the same formulation.

The embodiments of the invention in which an exclusive property or privilege is claimed are defined as follows:

1. An extended-life aqueous tissue histological fixative composition or solution comprising components expressed as approximate percent by weight based on total weight of the solution: glutaraldehyde, 5.5 to 10.0; a boric acid-borate buffer expressed as sodium tetraborate-$10H_2O$, 0.010 to 0.1, and boric acid, 0.120 to 0.6; a buffer stabilizer comprising one or more water soluble ascorbic acid compounds expressed as ascorbic acid, 0.100 to 0.8; and a metal complexing agent comprising one or more water soluble citric acid compounds expressed as sodium citrate, 0.06 to 1.0; and water to make 100%.

2. The tissue fixative solution of claim 1 having a pH in the range from about 5.8 to about 7.0.

3. The tissue fixative solution of claim 1 wherein the stabilizer comprises ascorbic acid.

4. The tissue fixative solution of claim 1 wherein the complexing agent comprises a citric acid alkali metal salt.

5. A concentrated tissue fixative solution dilutable with water to provide a ready-to-use solution according to claim 1.

6. A tissue fixative solution according to claim 1 comprising the following constituted components expressed as approximate percent by weight based on total weight of the solution:

| | |
|---|---|
| Glutaraldehyde | 5.5 to 10.0 |
| NaOH | 0.012 to 0.06 |
| Sodium tetraborate.$10H_2O$ | 0.010 to 0.1 |
| Boric acid | 0.120 to 0.6 |
| Ascorbic Acid | 0.100 to 0.8 |
| Sodium citrate | 0.06 to 1.0 |
| Water | To make 100.0 |

7. The tissue fixative solution of claim 1 containing a compatible surfactant.

8. The tissue fixative solution of claim 7 wherein the surfactant comprises at least one member of the group consisting of solution soluble $C_{5-11}$ fatty acids and salts thereof.

9. The tissue fixative solution of claim 8 wherein the quantity of surfactant is sufficient to provide solution surface tension in the range from about 7 to about 20 dynes per centimeter.

10. The tissue fixative solution of claim 8 wherein the surfactant is an n-caproic acid salt compound.

11. The tissue fixative solution of claim 8 wherein the surfactant is a heptanoic acid salt compound.

12. The tissue fixative solution of claim 8 wherein the surfactant is a caprylic acid salt compound.

13. In a histological method of preparing tissue for dehydrating, cutting, and staining, the step comprising subjecting specimen tissue prior to dehydration to preservation with tissue fixative solution as defined in claim 1 until fixed.

14. A method according to claim 13 comprising preparing the tissue fixative solution by dilution with water of a storage stable dilutable tissue fixative concentrate containing 30 to 35% by weight of glutaraldehyde.

* * * * *